United States Patent
Parkos et al.

(10) Patent No.: US 8,616,077 B2
(45) Date of Patent: Dec. 31, 2013

(54) NON-DESTRUCTIVE INSPECTION METHOD FOR METALLIC ALLOYS

(75) Inventors: Joseph Parkos, East Haddam, CT (US); Daniel A. Bales, Avon, CT (US); Mimi Nguyen-Vu, Berlin, CT (US); Gary M. Lomasney, Glastonbury, CT (US); Philip H. Ratliff, Cheshire, CT (US)

(73) Assignee: United Technologies Corporation, Hartford, CT (US)

( * ) Notice: Subject to any disclaimer, the term of this patent is extended or adjusted under 35 U.S.C. 154(b) by 777 days.

(21) Appl. No.: 12/535,896

(22) Filed: Aug. 5, 2009

(65) Prior Publication Data

US 2011/0030456 A1     Feb. 10, 2011

(51) Int. Cl.
*G01N 21/66* (2006.01)

(52) U.S. Cl.
USPC .................. 73/866; 423/98; 436/171

(58) Field of Classification Search
USPC .................. 73/866; 423/98; 436/171
See application file for complete search history.

(56) References Cited

U.S. PATENT DOCUMENTS

| | | | |
|---|---|---|---|
| 3,701,631 A | 10/1972 | Wilson | |
| 4,886,552 A | 12/1989 | Jaworowski et al. | |
| 5,334,834 A | 8/1994 | Ito et al. | |
| 5,827,413 A * | 10/1998 | Yamaguchi et al. | 204/293 |
| 5,993,559 A * | 11/1999 | Singer et al. | 134/2 |
| 6,176,999 B1 | 1/2001 | Jaworowski et al. | |
| 6,287,182 B1 | 9/2001 | Dwyer | |
| 6,627,833 B2 | 9/2003 | Varsell et al. | |
| 2004/0232584 A1 | 11/2004 | Johnson | |
| 2007/0292991 A1 | 12/2007 | Helberg et al. | |

FOREIGN PATENT DOCUMENTS

| | | |
|---|---|---|
| DE | 19718401 | 11/1997 |
| EP | 0998673 | 2/1999 |
| JP | 11326280 | 11/1999 |
| JP | 20008093615 | 4/2008 |
| WO | 20080143170 | 11/2008 |

OTHER PUBLICATIONS

EP Search Report dated Nov. 22, 2010.

* cited by examiner

*Primary Examiner* — Hezron E Williams
*Assistant Examiner* — Paul West
(74) *Attorney, Agent, or Firm* — Carlson, Gaskey & Olds, P.C.

(57) ABSTRACT

A non-destructive inspection method for detecting the presence of a contaminant that has alloyed with a metallic alloy of a part includes exposing the metallic alloy of the part to an extraction solution. The extraction solution extracts at least a portion of any of the contaminant that has alloyed with the metallic alloy. The extraction solution can then be analyzed to determine whether the solution includes any of the contaminant element, which indicates whether the part includes any of the contaminant element.

9 Claims, 1 Drawing Sheet

NON-DESTRUCTIVE INSPECTION METHOD FOR METALLIC ALLOYS

BACKGROUND OF THE INVENTION

This disclosure relates to inspecting metallic alloy parts to determine whether the parts include contaminant elements.

Nickel or other metallic alloys are typically used for parts that operate under relatively severe conditions, such as corrosive, elevated temperature, or high stress conditions. The composition of the nickel alloy may be selected to provide desirable properties, depending on the particular operating conditions. However, the nickel alloy may be exposed, through the manufacturing process of the part, to substances that can influence the desired properties.

SUMMARY OF THE INVENTION

An exemplary non-destructive inspection method for detecting the presence of a contaminant element that has alloyed with a metallic alloy of a part includes exposing the alloy of the part to an extraction solution. The extraction solution extracts at least a portion of any of the contaminant element that has alloyed with the metallic alloy. The extraction solution can then be analyzed to determine whether the solution includes any of the contaminant element.

In another aspect, a non-destructive inspection method for detecting the presence of a tin contaminant that has alloyed with a nickel alloy of an airfoil part includes injecting a hydrochloric acid solution into an internal cavity of the airfoil part to expose the internal cavity to the hydrochloric acid solution for a time that is suitable to avoid chemical attack of the nickel alloy. The hydrochloric acid solution extracts at least a portion of any tin contaminant. The hydrochloric acid solution can then be analyzed, e.g., by inductively coupled plasma (ICP) analysis to determine whether the hydrochloric acid solution includes any of the tin contaminant, to thereby determine whether the airfoil part includes the tin contaminant.

BRIEF DESCRIPTION OF THE DRAWINGS

The various features and advantages of the disclosed examples will become apparent to those skilled in the art from the following detailed description. The drawings that accompany the detailed description can be briefly described as follows.

DETAILED DESCRIPTION OF THE PREFERRED EMBODIMENT

Figure 1:
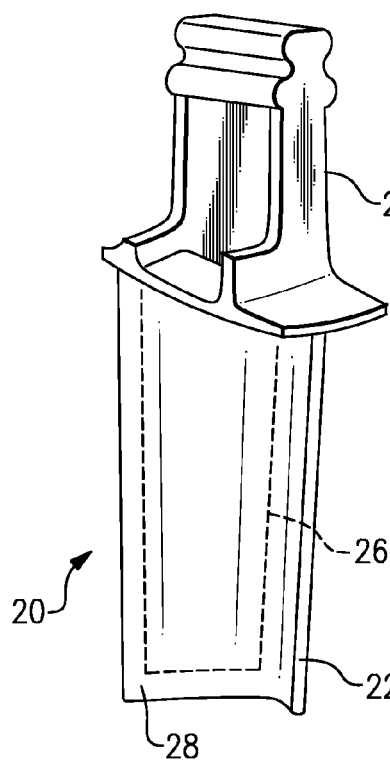
FIG. 1 illustrates an example part for non-destructive inspection.
Figure 2:
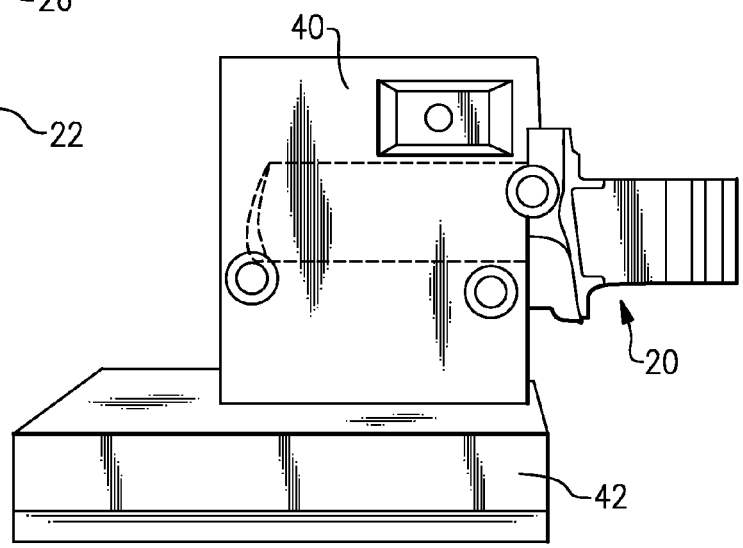
FIG. 2 illustrates the part mounted in a mounting block.

FIG. 1 illustrates an example part 20 that is formed from a metallic alloy material. The alloy may be any type of alloy desired for use in the part 20, such as a nickel alloy or cobalt alloy. In this example, the part 20 is an airfoil turbine blade for use in a gas turbine engine. However, in other examples, the part may be another type of nickel alloy part for use in other applications.

In the illustrated example, the part 20 includes an airfoil section 22 that is connected to a root section 24 for mounting the part 20 in a gas turbine engine. The airfoil section 22 may include an internal cavity 26 for receiving a cooling fluid in a known manner, such as bleed air from a compressor section of a gas turbine engine, to facilitate cooling the part 20 during use. As shown, the part 20 is a finished part and may be ready for assembly into a gas turbine engine. In this regard, the part 20 may be new or used.

The part 20 includes a protective coating 28 at least on the outer surface of the airfoil section 22 to protect the underlying alloy from erosion, corrosion, or the like during operation. As an example, the protective coating 28 may include an aluminide coating, an MCrAlY coating, or other type of protective coating. In the MCrAlY coating, the M includes at least one of nickel, cobalt, iron, or a combination thereof, Cr is chromium, Al is aluminum, and Y is yttrium or other active element. Given this description, one of ordinary skill in the art will recognize other types of protective coatings 28 that may be used.

The part 20 may undergo various operations during original manufacture, repair, or other stage in the life cycle of the part 20. For example, an operation might require rigidly mounting/holding the part 20. In this regard, the part 20 may be mounted in a block 40, which facilitates rigidly holding the part 20 for conducting the operation. For instance, the operation may include machining the root section 24 of the part 20. The block 40 may be attached to another piece 42 to facilitate holding the part 20.

The block 40 may be formed from a low melting alloy (LMA), that is an alloy with a low melting temperature, relative to the alloy of the part 20. For instance, the LMA may be a bismuth-tin alloy. After the operation is completed, the mounting block 40 is removed by heating and melting the LMA. The part 20 may then be rinsed in a cleaning solution, such as a suitable acidic solution that reacts with the LMA but does not harm the alloy, to remove any residual LMA.

The removal process normally removes all of the LMA from the part 20. However, trace amounts of the LMA may remain on the part 20 and diffuse into the alloy in elemental form or to form compounds with elements of the alloy, e.g., during subsequent thermal treatment. The part 20 is typically subjected to thermal treatment during or after application of the protective coating 28 or after a machining operation, for example. Thus, a premise of this disclosure is that the tin of the LMA may diffuse into the part 20 in elemental form or alloy to form undesired tin compounds, each of which may be difficult to detect in small amounts. As an example, the estimated total amount of the tin that may diffuse into the part 20 is only about 0.1 milligrams, if even present at all. Moreover, if the tin forms compounds, the tin is difficult to remove from the part 20 or detect without destroying the part. Thus, known inspection techniques, such as atomic absorption, that may typically be used to detect such elements/compounds are not suitable for detection.

Figure 3:
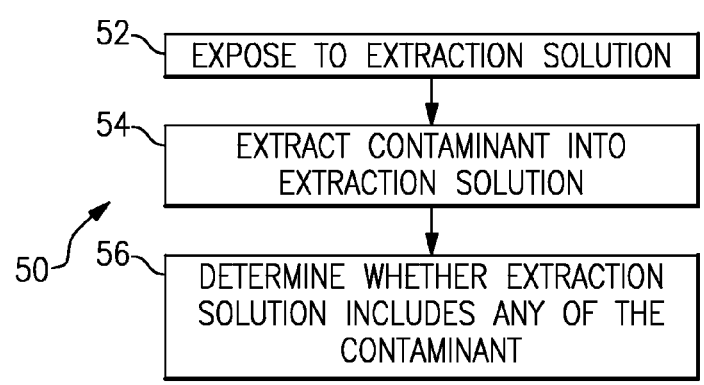
FIG. 3 illustrates an example non-destructive inspection method for detecting the presence of a contaminant element that has alloyed with a nickel alloy of a part.

FIG. 3 illustrates an example non-destructive inspection method 50 for detecting the presence of a contaminant element, such as tin, that has alloyed with the metallic alloy of the part 20. As an example, "non-destructive" may refer to evaluation of the part 20 without causing harm such that the part 20 can be used for its intended function, i.e., without a change in the performance due to the inspection. In this example, the method 50 generally includes three steps, an exposure step 52, an extraction step 54, and an analysis step 56. For the purpose of this example, the metallic alloy of the part 20 is a nickel alloy.

The exposure step 52 may include exposing the nickel alloy of the part 20 to an extraction solution. Some or all of the surfaces of the part 20 may be exposed to the extraction solution, depending on the type of the part 20. The extraction solution and exposure conditions may be controlled such that the solution does not chemically attack the alloy of the part 20, as will be described below.

The extraction solution leaches the contaminant element, if present, out from the alloy in the extraction step 54. The contaminant element may be in elemental form dissolved in the solution or in the compound form. The extraction solution can then be analyzed to determine whether the solution includes any of the contaminant element. The presence of the contaminant in the extraction solution indicates that the part 20 includes the contaminant element.

In another example that is more specific to a nickel alloy airfoil, the extraction solution may be a hydrochloric acid solution. For instance, the acid concentration of the hydrochloric acid solution and exposure time may be controlled to avoid chemical attack on the nickel alloy of the airfoil. As an example, the acid concentration may be 50% and the exposure time may be less than about two hours. In a further example, the exposure time may be about 30 minutes. Exposure times of more than two hours may result in chemical attack that oxidizes the alloy and materially changes the properties.

The airfoil may be masked to shield the protective coating 28 from exposure to the hydrochloric acid solution. For instance, any openings on the outer surface of the part connecting to the internal cavity 26 in the airfoil section 22 may be covered, e.g., using a suitable tape or other masking agent. Additionally, all or a portion of the airfoil section 22 may be sealed within a plastic cover or the like such that only the root section 24, which does not include the protective coating 28, is exposed. The masking, plastic cover and sealing may depend on the design of the remainder of the part and access to the internal cavity 26.

In some examples, the hydrochloric acid solution may be injected into the internal cavity 26 to expose the nickel alloy of the airfoil to the solution. That is, the outside of the airfoil cannot be exposed to the hydrochloric acid solution because the solution may chemically attack the protective coating 28. However, the surfaces of the internal cavity 26 generally do not include the protective coating 28 and are therefore suitable for exposure to the solution, which does not readily react with the nickel alloy in the given concentration and exposure time. In some cases, portions of the internal cavity 26 may include the protective coating 28, but the coating is not required and removal via the hydrochloric acid solution is acceptable.

The shape of the internal cavity 26 may vary, e.g., depending on the design of the part. In some examples, the internal cavity 26 may be a completely open cavity. In other examples, the internal cavity 26 may be a serpentine passage extending between the root section 24 and the tip of the airfoil section 22. In any case, all of the surfaces of the internal cavity 26 can be exposed to the hydrochloric acid solution to facilitate extracting any of the tin contaminant. In this regard, the hydrochloric acid solution may be injected with force into the internal cavity 26. For example, a syringe may be used to manually or automatically inject the hydrochloric acid solution. Optionally, a tube such as a polytetrafluoroethylene tube, may be connected to an orifice in the tip of the airfoil section 22 to inject the hydrochloric acid solution. The injection force causes the solution to flow throughout the internal cavity 26. In some cases, the force may facilitate flow of the solution through the serpentine passage where gravity alone would be inadequate.

Once injected, the hydrochloric acid solution remains in the internal cavity 26 for the selected exposure time. After the exposure time, the hydrochloric acid solution is drained from the internal cavity 26 into a beaker or other suitable container. The masking and plastic bag may then be removed and the airfoil may be washed to remove any residual hydrochloric acid solution from the internal cavity 26.

During exposure, the hydrochloric acid solution reacts with any of the tin contaminant or tin compounds near the surfaces of the internal cavity 26 to extract the tin contaminant from the nickel alloy into the hydrochloric acid solution. The relative amount of tin in the airfoil is small such that there may be ultra low levels of the tin contaminant at the surfaces of the internal cavity 26. Thus, if any tin contaminant is present, the concentration of the tin contaminant extracted into the hydrochloric acid solution may be only a few hundredths of one part per million, e.g., one to one-hundred parts per billion.

The hydrochloric acid solution that has been exposed to the nickel alloy is then analyzed in the analysis step 56 to determine whether the solution contains any of the tin contaminant. As an example, an inductively coupled plasma (ICP) analyzer may be used to analyze the hydrochloric acid solution and determine whether the solution includes any tin contaminant. In this case, since the amount of tin contaminant in the hydrochloric acid solution may be small, the ICP instrument may be adapted to provide a detection limit as low as 0.01 parts per million. Generally, ICP instruments generate a plasma such that elements within a sample emit characteristic, wavelength-specific light that can be measured to detect the elements.

Prior to subjecting the solution to the ICP analysis, the solution may be diluted to a lower concentration level to avoid harming the ICP equipment. In one example, the solution is diluted to a 15% acid concentration.

Parameters of the ICP equipment may be adjusted to facilitate providing a desired detection limit. For instance, the nebulizer, power supply, gas flow, sample introduction tube, torch, and cyclonic chamber may be adjusted to provide the 0.01 ppm detection limit desired to analyze the hydrochloric acid solution. In a more specific example, a user may analyze the hydrochloric acid solution using the following steps with the ICP equipment:

(a) Transfer the hydrochloric acid solution sample to a suitable graduated vessel;

(b) Within 24 hours, dilute the solution with deionized water to a final volume, which may be three times the original volume, and analyze the solution within two weeks;

(c) Inspect the solution for the presence of any particulate or foreign material, and filter the solution through a suitable filter of grade 40 or finer to remove any particulate matter;

(d) Calibrate the ICP instrument for tin analysis using (i) a clean baseline solution of 5% by volume hydrochloric acid to establish a zero point and (ii) a standard one part per million tin solution to establish the top end of the calibrated range. In addition, tin control solutions of concentrations of 0.02 ppm and 0.05 ppm may be analyzed during each processing cycle to validate test sample readings. A process solution blank, formulated by diluting a sample of clean hydrochloric acid solution by three times, may also be analyzed to identify any potential background contamination.

(e) Conduct three iterations of the ICP analysis on the sample hydrochloric acid solution and average the three test results. A single over-threshold reading may be cause for rejection.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A non-destructive inspection method for detecting the presence of a tin contaminant that has alloyed with a nickel-alloy of a part, comprising:
   (a) injecting a hydrochloric acid solution into an internal cavity of the part to expose the internal cavity to the hydrochloric acid solution for less than two hours to avoid chemical attack of the hydrochloric acid solution on the nickel-alloy, without exposing an outer portion of the part that has a protective coating thereon to the hydrochloric acid solution;
   (b) extracting at least a portion of any tin contaminant that has alloyed with the nickel-alloy into the hydrochloric acid solution; and
   (c) subjecting the hydrochloric acid solution that has been exposed to the nickel-alloy to inductively coupled plasma (ICP) analysis to determine whether the hydrochloric acid solution includes any of the tin contaminant, to thereby determine whether the part includes the tin contaminant.

2. A non-destructive inspection method for detecting the presence of a tin contaminant that has alloyed with a nickel-alloy of a part, comprising:
   (a) injecting a hydrochloric acid solution into an internal cavity of the part to expose the internal cavity to the hydrochloric acid solution for less than two hours to avoid chemical attack of the hydrochloric acid solution on the nickel-alloy, wherein the hydrochloric acid solution is a 50% acid concentration;
   (b) extracting at least a portion of any tin contaminate that has alloyed with the nickel-alloy into the hydrochloric acid solution; and
   (c) subjecting the hydrochloric acid solution that has been exposed to the nickel-alloy to inductively coupled plasma (ICP) analysis to determine whether the hydrochloric acid solution includes any of the tin contaminant, to thereby determine whether the part includes the tin contaminant.

3. A non-destructive inspection method for detecting the presence of a tin contaminant that has alloyed with a nickel-alloy of a part, comprising:
   (a) injecting a hydrochloric acid solution into an internal cavity of the part to expose the internal cavity to the hydrochloric acid solution for a time that is suitable to avoid chemical attack of the hydrochloric acid solution on the nickel-alloy by oxidation of the nickel-alloy and materially changing the properties of the nickel-alloy, including injecting the hydrochloric acid solution using a syringe to force the hydrochloric acid solution into the internal cavity of the part;
   (b) extracting at least a portion of any tin contaminant that has alloyed with the nickel-alloy into the hydrochloric acid solution; and
   (c) subjecting the hydrochloric acid solution that has been exposed to the nickel-alloy to inductively coupled plasma (ICP) analysis to determine whether the hydrochloric acid solution includes any of the tin contaminant, to thereby determine whether the part includes the tin contaminant.

4. The non-destructive inspection method as recited in claim 3, wherein step (a) includes masking an outer portion of the part to shield a protective coating on the outside from the hydrochloric acid solution.

5. The non-destructive inspection method as recited in claim 3, wherein step (a) includes exposing the hydrochloric acid solution for a time that is less than two hours.

6. The non-destructive inspection method as recited in claim 3, wherein step (c) includes detecting an amount as low as 0.01 parts per million of the tin contaminant in the hydrochloric acid solution.

7. The non-destructive inspection method as recited in claim 3, further including, prior to step (a), mounting the part in a mounting block that includes a low melt alloy having tin and subsequently, after removing the mounting block, conducting a heat treatment of the part such that any residual tin alloys with the nickel alloy.

8. The non-destructive inspection method as recited in claim 3, further including washing the part after step (b) to remove any residual hydrochloric acid solution within the internal cavity.

9. The non-destructive inspection method as recited in claim 3, further including diluting the hydrochloric acid solution prior to step (c) in preparation for subjecting the hydrochloric acid solution to the ICP analysis.

\* \* \* \* \*